United States Patent
Kammerer et al.

(10) Patent No.: US 10,759,800 B2
(45) Date of Patent: Sep. 1, 2020

(54) CRYSTALLINE FORMS OF DIAZABICYCLOOCTANE DERIVATIVES AND PRODUCTION PROCESS THEREOF

(71) Applicants: Fedora Pharmaceuticals Inc., Edmonton (CA); Meiji Seika Pharma Co., Ltd., Tokyo (JP)

(72) Inventors: Michael Kammerer, Basel (CH); Frederic Ran, Basel (CH)

(73) Assignees: FEDORA PHARMACEUTICALS INC., Alberta (CA); MEIJI SEIKA PHARMA CO., LTD., Tokyo (JP)

(*) Notice: Subject to any disclaimer, the term of this patent is extended or adjusted under 35 U.S.C. 154(b) by 0 days.

(21) Appl. No.: 16/140,601

(22) Filed: Sep. 25, 2018

(65) Prior Publication Data

US 2019/0092773 A1   Mar. 28, 2019

Related U.S. Application Data

(60) Provisional application No. 62/563,809, filed on Sep. 27, 2017.

(51) Int. Cl.
C07D 471/08 (2006.01)
A61P 31/04 (2006.01)

(52) U.S. Cl.
CPC ............ C07D 471/08 (2013.01); A61P 31/04 (2018.01); *C07B 2200/13* (2013.01)

(58) Field of Classification Search
CPC .................................................... C07D 471/08
USPC ....................................................... 514/300
See application file for complete search history.

(56) References Cited

U.S. PATENT DOCUMENTS

| | | | |
|---|---|---|---|
| 8,796,257 B2 | 8/2014 | Maiti et al. | |
| 9,181,250 B2 | 11/2015 | Abe et al. | |
| 2015/0203503 A1 | 7/2015 | Patil et al. | |
| 2016/0272641 A1* | 9/2016 | Abe | A61K 31/439 |

FOREIGN PATENT DOCUMENTS

| | | |
|---|---|---|
| CN | 101264088 | 9/2008 |
| EP | 0 438 747 | 7/1991 |
| EP | 1 448 234 | 8/2004 |
| EP | 3 067 355 | 9/2016 |
| EP | 3 228 620 | 10/2017 |
| WO | 2015/046207 | 4/2015 |
| WO | 2015/053297 | 4/2015 |
| WO | 2016/088863 | 6/2016 |
| WO | 2016/116878 | 7/2016 |
| WO | 2016/120752 | 8/2016 |
| WO | 2016/151543 | 9/2016 |

OTHER PUBLICATIONS

International Search Report and Written Opinion, dated Jan. 30, 2019, of international application No. PCT/IB2018/001185.
International Search Report and Written Opinion, dated Dec. 19, 2018, of international application No. PCT/IB2018/001187.
International Search Report and Written Opinion, dated Dec. 20, 2018, of international application No. PCT/IB2018/001204.
Baheti A. et al. "Excipients used in lyophilization of small molecules", J. Excipients Food Chem. 1(1):41-54 (2010).
Brittain H.G. et al. "Methods for the Characterization of Polymorphs", pp. 235 and 237 of Polymorphism in Pharmaceutical Solids, published by M. Dekker, New York, NY USA (1999).
Caira M.R. et al. "Crystalline Polymorphism of Organic Compounds" Topics in Current Chemistry 198:163-208 (1998).
Einfalt T. et al. "Methods of amorphization and investigation of the amorphous state" Acta Pharma. 63:305-334 (2013).
Kumar D.R. et al. "Formulation and Evaluation of (2013) Lyophilized Antibacterial Agent", Int. J. PharmTech Res. 5(4):1581-1589 (2013).
Morinaka et al., "OP0595, a new diazabicyclooctane: mode of action as a serine beta-lactamase inhibitor, antibiotic and beta-lactam 'enhancer'", J. Antimicrob. Chemo. 70:2779-2786 (2015).

* cited by examiner

*Primary Examiner* — Taofiq A Solola
(74) *Attorney, Agent, or Firm* — Wenderoth, Lind & Ponack, L.L.P.

(57) ABSTRACT

The present invention relates to crystalline forms of a diazabicyclooctane derivative represented by Compound I, the process for producing the same and methods for using the same:

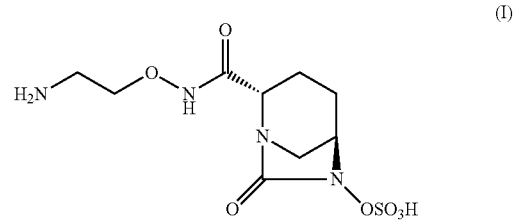

(I)

8 Claims, No Drawings

CRYSTALLINE FORMS OF DIAZABICYCLOOCTANE DERIVATIVES AND PRODUCTION PROCESS THEREOF

CROSS-REFERENCE TO RELATED APPLICATIONS

The present application claims the benefit of priority to U.S. Provisional Application No. 62/563,809 filed on Sep. 27, 2017, the entire contents of which is hereby incorporated by reference.

ACKNOWLEDGMENT OF GOVERNMENT SUPPORT

This invention was made with government support under Contract No. HHSO100201600038C awarded by the U.S. Department of Health and Human Services. The government has certain rights in the invention.

BACKGROUND

Penicillins and cephalosporins are β-lactam antibiotics that are widely and frequently used in the clinic. However, the acquisition of resistance to β-lactam antibiotics by various pathogens has had a damaging effect on maintaining the effective treatment of bacterial infections. The most significant known mechanism related to the acquisition of bacterial resistance is the production of class A, C, and D β-lactamases having a serine residue at the active center. These enzymes decompose the β-lactam antibiotic, resulting in the loss of the antimicrobial activities. Class A β-lactamases preferentially hydrolyze penicillins while class C β-lactamases have a substrate profile favoring cephalosporins.

Commercially available β-lactamase inhibitors, e.g., clavulanic acid, sulbactam and tazobactam are known and these inhibitors are effective mainly against class A β-lactamase producing bacteria, and used as a mixture with a penicillin antibiotic. However, 250 types or more of β-lactamases have been reported to date, including resistant bacteria which produce class A KPC-2 β-lactamase decomposing even carbapenem.

In recent years, infectious diseases caused by the above-mentioned resistant bacteria as pathogenic bacteria are found not only in severe infectious disease but also occasionally in community-acquired infectious disease. The currently available β-lactamase inhibitors are insufficient to inhibit the incessantly increasing β-lactamase and novel β-lactamase inhibitors which are required for the difficult treatment of bacterial infectious diseases caused by resistant bacteria. The development of antibacterial agents as well as β-lactamase inhibitors is in strong demand as the commercially available inhibitors become increasingly ineffective.

The present application is directed to crystalline forms of an antibacterial agent and β-lactamase inhibitor, useful in the treatment of infectious diseases. Specifically, (2S, 5R)—N-(2-aminoethoxy)-7-oxo-6-(sulfooxy)-1,6-diazabicyclo[3.2.1]octane-2-carboxamide, represented by Compound (I), is a "potent, broad-spectrum, non-β-lactam β-lactamase inhibitor" useful for antibiotic-resistant Gram-negative bacteria (Li, H.; Estabrook, M.; Jacoby, G. A.; Nichols, W. W.; Testa, R. T.; Bush, K. *Antimicrob Agents Chemother* 2015, 59, 1789-1793.) There are four crystalline forms of (2S, 5R)—N-(2-aminoethoxy)-7-oxo-6-(sulfooxy)-1,6-diazabicyclo[3.2.1]octane-2-carboxamide previously reported and known in the art (see, e.g., International Publication no. WO 2015/053297).

When developing technologies for a commercial process, there are several factors and properties to consider when converting a small-scale lab process to a large manufacturing process suitable for clinical use. One such factor includes solid state physical properties, which entails the flowability of the milled solid, rate of dissolution and stability. The physical characteristics are influenced by the conformation and orientation of molecules in the unit cell, which defines a particular crystalline form of a substance. A crystalline form may give rise to thermal behavior different from that of the amorphous material or another crystalline form. Thermal behavior is measured in the laboratory using techniques such as capillary melting point, thermogravimetric analysis (TGA) and differential scanning calorimetry (DSC). These techniques may be used to distinguish between different crystalline forms. A particular crystalline form may show distinct spectroscopic properties that can be detected using powder X-ray diffractometry (XRPD), nuclear magnetic resonance (NMR) spectrometry, Raman spectroscopy and infrared (IR) spectrometry.

In deciding which crystalline form is preferable, the numerous properties of the crystalline forms must be compared and the preferred crystalline form chosen based on the many physical property variables. A particular crystalline form may be preferable in certain circumstances in which certain aspects, such as ease of preparation, stability, etc., are deemed to be critical. In other situations, a different crystalline form may be preferred for greater solubility and/or superior pharmacokinetics.

SUMMARY

The present application relates to crystalline forms V and VI of a diazabicyclooctane derivative represented by (2S, 5R)—N-(2-aminoethoxy)-7-oxo-6-(sulfooxy)-1,6-diazabicyclo[3.2.1]octane-2-carboxamide, also referred to as "Compound (I)," and a process for producing crystalline form V. Methods of treating bacterial infections by administering the crystalline form or forms are also described:

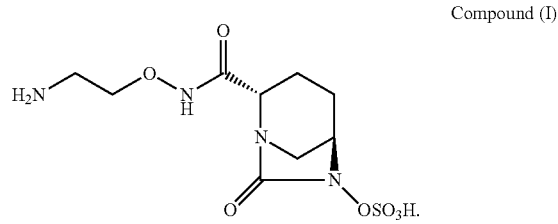

Compound (I)

In an aspect of the invention, the present application provides crystalline form V of Compound (I) characterized by an X-ray powder diffraction pattern having characteristic peaks expressed in values of degrees 2Θ at about 17.1, at about 18.8, and at about 20.2±0.2. In an embodiment, crystalline form V is characterized by an X-ray diffraction pattern having characteristic peaks expressed in values of degrees 2Θ at about 15.7 and about 23.1±0.2. In another embodiment, crystalline form V is characterized by an X-ray diffraction pattern having characteristic peaks expressed in values of degrees 2Θ at about 15.7; about 17.1; about 18.8; about 20.2; and about 23.1±0.2. In an embodiment, crystalline form V is characterized by an X-ray diffraction pattern having characteristic peaks expressed in values of degrees 2Θ at about 7.4; about 12.2; about 15.7; about 17.1; about 18.5; about 18.8; about 20.2; about 20.4; about 21.8; about 22.5; about 23.1; about 24.3; about 25.1; about 25.4; about 26.5; about 28.0; about 29.7; about 30.5; about 30.7; about 31.4; and about 34.1±0.2.

In an aspect of the invention, the present application provides a process for producing a crystalline form V of a compound represented by Compound (I):

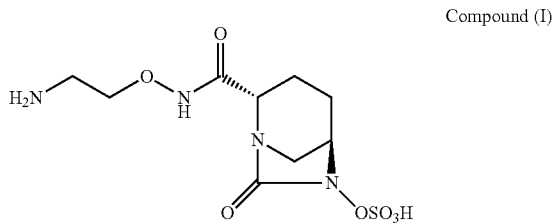

Compound (I)

comprising (a) dissolving crystalline form IV of Compound (I) in a solvent, to form a solution of Compound (I); (b) agitating the solution of Compound (I); (c) filtering by centrifugation of the solution of Compound (I); and (d) evaporating the solution to produce crystalline form V of Compound (I). In an embodiment, the solvent of step (a) is water, ethanol or a mixture thereof. In an embodiment, the agitation of the solution in step (b) occurs for at least 22 hours. In another embodiment, the process for producing crystalline form V of Compound (I) further comprises drying the crystalline form V of Compound (I) at 22±1° C. under a reduced pressure of no more than 5 mbar for at least 20 hours.

In an aspect of the invention, the present application provides a method for treating a bacterial infection in a subject in need thereof comprising administering to the subject a therapeutically effective amount of crystalline form V of Compound (I). In an embodiment, the subject in need thereof is a human.

In another aspect, the application provides a pharmaceutical composition comprising crystalline form V of Compound (I) and a pharmaceutically acceptable carrier, pharmaceutical excipient or pharmaceutical diluent. In an embodiment, the method for treating a bacterial infection in a subject in need thereof comprises administering to the subject the pharmaceutical composition in amount sufficient to inhibit a bacterial beta-lactamase.

In an aspect, the application provides a method for treating a bacterial infection in a subject in need thereof comprising administering to the subject a therapeutically effective amount of a crystalline form V of Compound (I) and a therapeutically effective amount of a β-lactam antibiotic. In an embodiment, the β-lactam antibiotic is a penicillin. In another embodiment, the β-lactam antibiotic is a cephalosporin. In an embodiment, the β-lactam antibiotic is a monobactam. In a further embodiment, the subject in need thereof is a human.

In another aspect of the invention, the present application provides crystalline form VI of Compound (I) characterized by an X-ray powder diffraction pattern having characteristic peaks expressed in values of degrees 2Θ at about 16.7; about 22.4; and about 23.7±0.2. In an embodiment, crystalline form VI is characterized by an X-ray diffraction pattern having characteristic peaks expressed in values of degrees 2Θ at about 14.3 and about 17.2±0.2. In another embodiment, crystalline form VI is characterized by an X-ray diffraction pattern having characteristic peaks expressed in values of degrees 2Θ at about 14.3; about 16.7; about 17.2; about 22.4; and about 23.7±0.2 degrees 2Θ. In an embodiment, crystalline form VI is characterized by an X-ray diffraction pattern having characteristic peaks expressed in values of degrees 2Θ at about 7.9; about 11.0; about 11.7; about 13.5; about 14.3; about 16.7; about 17.2; about 18.9; about 20.1; about 21.4; about 22.0; about 22.4; about 22.7; about 23.5; about 23.7; about 24.5; about 25.0; about 27.1; about 27.4; about 28.0; about 31.2; about 31.8; and about 35.6±0.2.

In another embodiment the β-lactam is a β-lactam antibiotic and comprises a core selected from penam, carbapenam, oxapenam, penem, carbapenem, monobactam, cephem, carbacephem and oxacephem.

In another embodiment the β-lactam antibiotic is selected from ampicillin, amoxicillin, azidocillin, azlocillin, aztreonam, biapenem, carbeniccilin, carfecillin, carindacillin, carumonam, cefepime, cefotaxim, cefsumide, ceftaroline, ceftolozane ceftriaxone, ceftazidime, cephem, doripenem, ertapenem, flomoxef, meropenem, piperacillin, tazobactam, ticarcillin, and tigermonam, or pharmaceutically acceptable salts or esters thereof.

In yet another embodiment the β-lactam antibiotic is meropenem, or a pharmaceutically acceptable salt or ester thereof.

The compounds are useful in the treatment of bacterial infections in humans or animals either alone or in combination with β-lactam antibiotics and/or with other non β-lactam antibiotics.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

The crystalline forms of Compound (I) can exist in various isomeric forms, as well as in one or more tautomeric forms, including both single tautomers and mixtures of tautomers. The term "isomer" is intended to encompass all isomeric forms of a compound of this invention, including tautomeric forms of the compound. The term "tautomer" refers to a proton shift from one atom of a molecule to another atom of the same molecule.

Crystalline forms of Compound (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A crystalline form of Compound (I) can be in the form of an optical isomer or a diastereomer. Accordingly, the invention encompasses crystalline forms of Compound (I) and their uses as described herein in the form of their optical isomers, diastereoisomers and mixtures thereof, including a racemic mixture. Optical isomers of the crystalline forms can be obtained by known techniques such as asymmetric synthesis, chiral chromatography, or via chemical separation of stereoisomers through the employment of optically active resolving agents.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another. Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Throughout the present application, Compound (I) is used interchangeably with (2S, 5R)—N-(2-aminoethoxy)-7-oxo-6-(sulfooxy)-1,6-diazabicyclo[3.2.1]octane-2-carboxamide. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with an infectious disease. In certain embodiments, such terms refer to minimizing the spread or worsening of the infectious disease resulting from the administration of one or more prophylactic or therapeutic agents to a patient with such an infectious disease.

The term "effective amount" refers to an amount of a compound of the invention or other active ingredient sufficient to provide a therapeutic or prophylactic benefit in the treatment or prevention of an infectious disease or to delay or minimize symptoms associated with an infectious disease. Further, a therapeutically effective amount with respect to crystalline forms of Compound (I) means that amount of therapeutic agent alone, or in combination with other therapies, that provides a therapeutic benefit in the treatment or prevention of an infectious disease. Used in connection with crystalline forms of Compound (I), the term can encompass an amount that improves overall therapy, reduces or avoids symptoms or causes of disease, or enhances the therapeutic efficacy or synergies with another therapeutic agent. The amount of a crystalline form of Compound (I) which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient must undergo chemical conversion by metabolic processes before becoming an active pharmacological agent. Exemplary prodrugs of crystalline forms of Compound (I) are esters, acetamides, and amides.

The crystalline forms of Compound (I) may be isotopically-labelled by having one or more atoms replaced by an atom having a different atomic mass or mass number. Examples of isotopes that can be incorporated Compound (I), include isotopes of hydrogen, carbon, nitrogen, oxygen, phosphorous, fluorine, chlorine, or iodine. Illustrative of such isotopes are $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled crystalline forms of Compound (I), therefore, are useful in drug and/or tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}C$, $^{18}F$, $^{15}O$ and $^{13}N$, provides labeled analogs of the inventive compounds that are useful in Positron Emission Tomography (PET) studies, e.g., for examining substrate receptor occupancy. Isotopically-labeled crystalline forms of Compound (I) can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of Compound (I). Such products may result from, for example, the oxidation, reduction, hydrolysis, amidation, esterification, dimerization and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of crystalline forms V and VI of Compound (I). Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the crystalline forms of Compound (I). As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the crystalline forms of Compound (I) may exist as a hydrate, including a monohydrate, dihydrate, hemihydrate, sesquihydrate, trihydrate, tetrahydrate and the like, as well as the corresponding solvated forms. The crystalline forms of Compound (I) may be true solvates, while in other cases, the compounds of the invention may merely retain adventitious water or be a mixture of water plus some adventitious solvent.

One skilled in the art will understand that the relative intensities and positions of the peaks obtained by X-ray powder diffraction may vary depending upon factors such as, the sample preparation technique, the sample mounting procedure and the particular instrument employed. For example, in additional embodiments, the listed X-ray powder diffraction pattern peaks for the crystalline forms of Compound (I) may be about ±0.2 degrees 2Θ.

It is known that an X-ray powder diffraction pattern may be obtained which has one or more measurement errors depending on measurement conditions (such as equipment or machine used). Intensities in an X-ray powder diffraction pattern may fluctuate depending on measurement conditions. Therefore, it should be understood that the crystalline forms of the present invention are not limited to the crystals that provide X-ray powder diffraction patterns identical to the X-ray powder diffraction patterns described in this application, and any crystals providing X-ray powder diffraction patterns substantially the same as those described in the application fall within the scope of the present invention. For example, relative intensity of peaks can be affected by grains above 30 microns in size and non-unitary aspect ratios, which may affect analysis of samples. A person skilled in the art will recognize that the position of reflections can be affected by the precise height at which the sample sits in the diffractometer and the zero calibration of the diffractometer. The surface planarity of the sample may also have a small effect. Therefore, the diffraction pattern data described herein are not to be taken as absolute values. (Jenkins, R & Snyder, R. L. "Introduction to X-Ray Powder Diffractometry" John Wiley & Sons 1996; Bunn, C. W. (1948), Chemical Crystallography, Clarendon Press, London; Klug, H. P. & Alexander, L. E. (1974), X-Ray Diffraction Procedures).

In some embodiments, the experimental powder diffraction patterns were recorded at ambient conditions in transmission geometry with a Stoe Stadi P diffractometer (Cu Kα1 radiation [1.5406 Å], 40 kV and 40 mA, primary beam monochromator, silicon strip detector, angular range 3° to 42° 2Θ with a step size of 0.02° 2Θ, approximately 30 minutes total measurement time). The samples were prepared and analyzed without further processing (e.g., grinding or sieving) of the substance.

In some embodiments, the single crystal X-ray intensity data were collected at 293(2) K using a Gemini R Ultra diffractometer (Rigaku) with Cu—K-alpha-radiation (1.54184 Å) and processed with the Crysalis-package. Structure solution and refinement was performed using the ShelXTL software (Bruker AXS, Karlsruhe).

Generally, a measurement error of a diffraction angle in an X-ray powder diffractogram is plus or minus 0.2° 2Θ, and such degree of a measurement error should be taken into account when considering the X-ray powder diffraction patterns described in this application. Furthermore, it should be understood that intensities may fluctuate depending on experimental conditions and sample preparation (preferred orientation).

In one aspect, substantially pure crystalline forms of the present invention are provided. For example, the present invention includes crystalline forms V and VI of Compound (I) as described in this application that are about ≥95% pure. For example, the forms may be about ≥95%, ≥96%, ≥97%, ≥98% or ≥99% pure.

In some embodiments, crystalline forms V and VI of Compound (I) isolated in a substantially pure form. The Forms described herein may have purity of more than about 90%, about 91%, about 92%, about 93%, about 94%, about 95%, about 96%, about 97%, about 98%, or about 99% by weight. In a further embodiment, the forms may have a purity of more than about 95% by weight. For example, the forms may be ≥95%, ≥96%, ≥97%, ≥98% or ≥99% pure.

Pharmaceutical Formulations

In one embodiment, Compound (I), either crystalline form V or crystalline form VI is formulated as pharmaceutically acceptable compositions that contain the crystalline form in an amount effective to treat a particular disease or condition of interest upon administration of the pharmaceutical composition to a mammal. Pharmaceutical compositions in accordance with the present invention can comprise Compound (I), either crystalline form V or crystalline form VI in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining crystalline forms of Compound (I) with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a crystalline form of Compound (I) with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

Therapeutic Use

The crystalline forms of Compound (I), or their pharmaceutically acceptable salts or esters, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment of an infectious disease in the mammal. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

The crystalline forms of Compound (I), or pharmaceutically acceptable salts or esters thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The term "β-lactam antibiotic" refers to a compound with antibiotic property that contains a β-lactam functionality. Examples of β-lactam antibiotics which can be used in combination with the compounds of the present invention represented by Compound (I), crystalline forms V and VI are commonly marketed penicillins, cephalosporins, penems, carbapenems and monobactams.

Examples of β-lactam antibiotics which can be used in combination with the compounds of the present invention represented by Compound (I), crystalline forms V and VI are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine, latamoxef (moxalactam), and CXA-101. From the carbapenem class of β-lactam antibiotics such as imipenem, meropenem, panipenem, biapenem, doripenem, ertapenem and the like could be used. From monobactam class of β-lactam antibiotics such as aztreonam, carumonam, tigemonam, and the like could be used as the combination partner of antibiotic.

The crystalline forms of Compound (I) are synthesized using conventional synthetic methods, and more specifically using the general methods noted below. Specific synthetic protocols for several compounds in accordance with the present invention are described in the Examples.

Examples

The following examples are provided for purposes of illustration and not limitation.

The crystalline form V of Compound (I) was obtained through several steps as described. A closed vial was charged with 300 mg of polymorph crystalline form IV dissolved in 1.0 mL of water at 22° C. The solution was agitated at 25° C. for 22 hours. The solution was then filtered by centrifugation to remove microscopic particulates. The clear filtrate was separated and the solvent was allowed to evaporate at 40° C. under a continuous flow of $N_2$ for 2.5 hours. The solid was dried at 22° C. at less than 5 mbar for 20 hours to afford crystalline form V of Compound (I) (see Table 1 and Table 2).

In an alternate method, a closed vial was charged with a mixture of 200 mg of crystalline form IV of Compound (I) and 1.0 mL of a water/ethanol solution (54:46 w/w). The mixture was equilibrated under agitation at 40° C. for 22 hours. After equilibration, the suspension was separated by centrifugal filtration. The clear filtrate, which was recovered from the suspension, was separated and the solvent was allowed to evaporate at 40° C. under a continuous flow of $N_2$ for 3.5 hours to produce a wet solid. The wet solid was dried at 22° C. at less than 5 mbar for 20 hours to afford the crystalline form V.

The crystalline form VI of Compound (I) was obtained during the last reaction step of Compound (I) wherein the added water quantity was increased from 3 to 11 stoichiometric equivalents (see Table 3).

TABLE 1

Powder X-ray diffraction of crystalline form V of Compound (I)
Powder X-ray diffraction of crystalline form V

| Degree 2-theta | Relative intensity (%) |
|---|---|
| 7.4 | 14 |
| 12.2 | 12 |
| 15.7 | 51 |
| 17.1 | 100 |
| 18.5 | 24 |
| 18.8 | 61 |
| 20.2 | 76 |
| 20.4 | 29 |
| 21.8 | 11 |
| 22.5 | 25 |
| 23.1 | 54 |
| 24.3 | 23 |
| 25.1 | 13 |
| 25.4 | 22 |
| 26.5 | 16 |
| 28.0 | 12 |
| 29.7 | 26 |
| 30.5 | 21 |
| 30.7 | 11 |
| 31.4 | 13 |
| 34.1 | 10 |

TABLE 2

Single crystal structural data of crystalline form V of Compound (I)

| Crystalline form | Form V |
|---|---|
| Solid form description | Polymorph |
| Measuring Temperature | 293 (2) K |
| Crystal system | Monoclinic |
| Space group | P2(1) |
| Unit cell dimensions | |
| a= | 8.8157 (6) Å |
| b= | 6.4213 (4) Å |
| c= | 11.8868 (9) Å |
| α= | 90° |
| β= | 92.351 (6)° |

TABLE 2-continued

Single crystal structural data of crystalline form V of Compound (I)

| Crystalline form | Form V |
| --- | --- |
| γ= | 90° |
| Cell volume | 672.32 (8) Å$^3$ |
| API molecules in unit cell | 2 |
| Calculated density | 1.602 g/cm$^3$ |

TABLE 3

Powder X-ray diffraction of crystalline form VI of Compound (I)
Powder X-ray diffraction of crystalline form VI

| Degree 2-theta | Relative intensity (%) |
| --- | --- |
| 7.9 | 10 |
| 11.0 | 11 |
| 11.7 | 28 |
| 13.5 | 27 |
| 14.3 | 34 |
| 16.7 | 100 |
| 17.2 | 40 |
| 18.9 | 13 |
| 20.1 | 13 |
| 21.4 | 10 |
| 22.0 | 19 |
| 22.4 | 54 |
| 22.7 | 20 |
| 23.5 | 11 |
| 23.7 | 53 |
| 24.5 | 14 |
| 25.0 | 18 |
| 27.1 | 18 |
| 27.4 | 17 |
| 28.0 | 9 |
| 31.2 | 9 |
| 31.8 | 9 |
| 35.6 | 11 |

The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A crystalline form V of a compound represented by Compound (I):

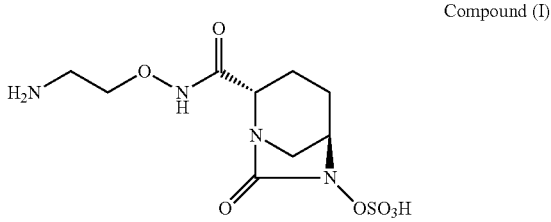

Compound (I)

having an X-ray powder diffraction pattern with characteristic peaks expressed in values of degrees 2Θ at about 17.1, about 18.8, and about 20.2±0.2.

2. The crystalline form V according to claim 1, wherein the X-ray powder diffraction pattern has characteristic peaks expressed in values of degrees 2Θ at about 15.7 and about 23.1±0.2.

3. The crystalline form V according to claim 1, wherein the X-ray powder diffraction pattern has characteristic peaks expressed in values of degrees 2Θ at about 15.7; about 17.1; about 18.8; about 20.2; and about 23.1±0.2.

4. The crystalline form V according to claim 1, wherein the X-ray powder diffraction pattern has characteristic peaks expressed in values of degrees 2Θ at about 7.4; about 12.2; about 15.7; about 17.1; about 18.5; about 18.8; about 20.2; about 20.4; about 21.8; about 22.5; about 23.1; about 24.3; about 25.1; about 25.4; about 26.5; about 28.0; about 29.7; about 30.5; about 30.7; about 31.4; and about 34.1±0.2.

5. A process for producing a crystalline form V of Compound (I) according to claim 1 comprising:
 (a) dissolving Compound (I) in a solvent, to form a solution of Compound (I);
 (b) agitating the solution of Compound (I);
 (c) centrifuging the solution of Compound (I); and,
 (d) evaporating the solution, to produce crystalline form V of Compound (I).

6. The process according to claim 5, wherein the solvent is water, ethanol, or a mixture thereof.

7. The process according to claim 5, wherein the agitation of the solution occurs for at least 22 hours.

8. The process according to claim 5 further comprising drying the crystalline form V of Compound (I) at 22±1° C. under a reduced pressure of no more than 5 mbar for at least 20 hours.

* * * * *